US011975091B2

(12) United States Patent
Son et al.

(10) Patent No.: US 11,975,091 B2
(45) Date of Patent: May 7, 2024

(54) COMPOSITION FOR ENHANCING PROTEIN STRENGTH

(71) Applicant: LG Household & Health Care Ltd., Seoul (KR)

(72) Inventors: Seong Kil Son, Daejeon (KR); Won Kyung Choi, Daejeon (KR); Dong Wan Kim, Daejeon (KR); Ji Hee Yoo, Daejeon (KR); Jeong Rae Lee, Daejeon (KR); Sang Min Lee, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 74 days.

(21) Appl. No.: 17/472,162

(22) Filed: Sep. 10, 2021

(65) Prior Publication Data
US 2021/0401714 A1 Dec. 30, 2021

Related U.S. Application Data

(63) Continuation of application No. 16/477,047, filed as application No. PCT/KR2017/014555 on Dec. 12, 2017, now abandoned.

(30) Foreign Application Priority Data

Jan. 11, 2017 (KR) .................. 10-2017-0004038
Nov. 29, 2017 (KR) .................. 10-2017-0161920

(51) Int. Cl.
*A61K 8/58* (2006.01)
*A61K 8/55* (2006.01)
*A61K 8/66* (2006.01)
*A61Q 5/00* (2006.01)
*A61Q 19/00* (2006.01)

(52) U.S. Cl.
CPC ............. *A61K 8/585* (2013.01); *A61K 8/55* (2013.01); *A61K 8/66* (2013.01); *A61Q 5/00* (2013.01); *A61Q 19/00* (2013.01)

(58) Field of Classification Search
CPC ...................................... A61K 8/585
See application file for complete search history.

(56) References Cited

U.S. PATENT DOCUMENTS

| 2009/0087398 A1 | 4/2009 | Brown et al. |
| 2011/0021679 A1* | 1/2011 | Takahashi ............ C08G 18/282 |
| | | 564/252 |
| 2011/0319627 A1 | 12/2011 | Pandey et al. |
| 2012/0277406 A1 | 11/2012 | Acemoglu et al. |
| 2014/0314696 A1 | 10/2014 | Kergosien et al. |
| 2018/0193236 A1* | 7/2018 | Son ........................ A61K 8/898 |

FOREIGN PATENT DOCUMENTS

| CN | 105813626 A | 7/2016 | |
| EP | 0159628 A2 | 10/1985 | |
| EP | 0159628 B1 * | 7/1990 | ............... A61K 7/11 |
| FR | 2955488 A1 | 7/2011 | |
| JP | H9110647 A | 4/1997 | |
| JP | 20007642 A | 1/2000 | |
| JP | 201174041 A | 4/2011 | |
| JP | 201591840 A | 5/2015 | |
| JP | 2016164158 A | 9/2016 | |
| KR | 20140096053 A | 8/2014 | |
| KR | 20140121772 A | 10/2014 | |
| KR | 101585343 B1 * | 1/2016 | ............... A61K 8/40 |
| KR | 101585343 B1 | 1/2016 | |
| WO | 2009043613 A1 | 4/2009 | |
| WO | 2016083578 A1 | 6/2016 | |

OTHER PUBLICATIONS

English machine translation of KR-10-1585343 B1 made on May 6, 2023. (Year: 2023).*
Search Report dated Dec. 8, 2021 from the Office Action for Chinese Application No. 201780082452.0 dated Dec. 16, 2021, 2 pages.
International Search Report for Application No. PCT/KR2017/014555 dated Apr. 13, 2018, 6 pages.
Search Report dated Dec. 16, 2021 from Office Action for Taiwan Office Action dated Dec. 20, 2021. 1 pg.

* cited by examiner

*Primary Examiner* — Michael B. Pallay
(74) *Attorney, Agent, or Firm* — Lerner David LLP

(57) ABSTRACT

A composition for enhancing protein strength according to the present invention contains an aminosilane compound capable of covalent binding with a protein of hair, scalp, skin, nails, leather, or textile, so that the protein and the amino silane compound form a covalent bond, and thus the composition can improve the protein strength enhancement effect and maximize the semi-permanent protein strength enhancement effect.

4 Claims, No Drawings

COMPOSITION FOR ENHANCING PROTEIN STRENGTH

CROSS-REFERENCE TO RELATED APPLICATIONS

The present application is a continuation of U.S. application Ser. No. 16/477,047 filed Jul. 10, 2019, a national phase entry under 35 U.S.C. § 371 of International Application No. PCT/KR2017/014555, filed Dec. 12, 2017, which claims priority to Korean Patent Application No. 10-2017-0004038, filed Jan. 11, 2017 and Korean Patent Application No. 10-2017-0161920, filed Nov. 29, 2017, the disclosure of all of which are incorporated herein by reference.

TECHNICAL FIELD

The present invention relates to a composition for enhancing protein strength of hair, skin, finger/toe nails, leather or fiber.

BACKGROUND ART

The skin is tissue covering the surface of a body, consisting of the epidermis, the dermis and a subcutaneous fat layer, and skin appendages include a sweat gland, a sebaceous gland, hair, and hand/toe nails. The epidermis constituting the outermost part of the skin is derived from the ectoderm, and largely consists of an inner part formed of living cells called the malpighian layer, and an outer part, the stratum corneum, formed of anucleate, flat, dry and dead cells. The thicknesses of the skin are about 0.03 mm at a face part, about 0.16 to 0.8 mm at the palms and soles of feet, and about 0.1 mm at an eyelid, which is the thinnest part. The epidermis is generally the stratified squamous cornified epithelium, mainly consisting of keratinocytes, and also including melanocytes, Langerhans cells and Merkel cells.

The keratinocyte is the main component of the epidermis, which is divided into four layers such as the cornified layer (the outermost layer), the granular layer, the spinous layer and the basal layer, and there is a translucent layer between the cornified layer and the granular layer at the soles of palms and feet.

Millions of new cells are formed every day in the epidermis, and continue to be shed from the outermost part of the epidermis without staying in one place. Here, these cells gradually turn into rigid keratin when being shed from the cells. The cells of the epidermis are first made in the basal layer, and their shapes and functions are also changed while gradually rising toward the surface.

The epidermis is gradually transformed into the basal layer, the spinous layer, the granular layer and the cornified layer as keratinized, and all of these cells are cells made during keratogenesis, and thus called keratinocytes.

A differentiation process in the keratinocytes is performed through four steps: 1) division of basal cells, 2) synthesis and alignment in spinous cells, 3) self-degradation in granular cells, and 4) reconstruction in corneocytes, and in the final step of differentiation, the cornified layer is formed. This process is called keratinization.

The life span of keratinocytes is about 28 days, and although slightly varying from site to site, millions of keratinocytes are detached every day, and millions of new cells are generated from the underlying layer. On the skin surface of the human body, aging keratinocytes are continuously being shed, and in aged skin, it takes more time for the detachment of the cornified layer, resulting in thickening of the cornified layer. Therefore, the functional degradation of keratinocytes leads to generation of more dead cells, and causes fine lines and skin roughness.

The cornified layer is a part forming keratin, which is the outermost, rigid, dry and thin layer, and consisting of 20 to 25 layers. The cornified layer is the name given due to the fact that a protein consists of keratin made by changing a protein to be rigid. As it is close to the skin surface, the cornified layer has a flat and long shape. The main components of the cornified layer include the keratin protein (58%), a lipid (11%), a natural moisturizing factor (NMF, 38%). The thickness of the cornified layer varies depending on a body part, and the palms or soles have very thick cornified layers and thus they can withstand physical impact, friction or trauma which is received in daily life. Although the cornified layer consists of anucleate, dead cells and keratin protein, it is most important in terms of skin protection. The cornified layer plays an important role in preventing external bacteria or foreign toxic substances from entering the body, and dehydration of the body. The main component of the cornified layer is the keratin protein (58%), consisting of amino acids such as glycine, alanine, valine, leucine, isoleucine, threonine, serine, cysteine, cystine, methionine, aspartic acid, asparagine, glutamic acid, diiodotyrosine, lysine, arginine, histidine, phenylalanine, tyrosine, tryptophan, proline and oxyproline, and particularly, the keratin constituted in the cornified layer includes about 6.4 to 8.1% of aspartic acid, about 9.1 to 15.4% of glutamic acid, and about 3.1 to 6.9% of lysine.

Generally, hair is a keratinized structure formed by embryological depression of the epithelium, and corresponds to one of the skin appendages including a sweat gland and a sebaceous gland. Hair refers to the coat covering the outside of the human body, including the hair on the head, soft hair, mustaches or beards, the hair under the arms, pubic hair, etc., and in some cases, only refers to hair on the scalp.

Hair consists of the keratin protein which is the same as the main component of the cornified layer, and keratin is largely classified into two according to origin. The keratin constituting the cornified layer is called soft keratin, and keratin constituting hair and finger nails is called hard keratin. The keratin is divided due to the difference in content of cysteine, which is one of the amino acids, and the hard keratin has a high cysteine content, and the soft keratin has a low cysteine content. Therefore, the hard keratin is highly resistant to an external stimulus or the penetration of a chemical substance.

A hair fiber has a thickness of about 50 to 100 μm, consists of a cuticle and a cortex, and sometimes, further includes a medulla, present in the middle of the hair fiber. All of these cells are dead cells, and most of them are filled with the keratin protein.

Human hair consists of about 65 to 95% of the keratin protein, and includes water and lipids (binding and unbinding types), a pigment, and trace elements. The protein is formed of mixtures of about 20 to 50 amino acids in a long chain, and each chain is wound in a helical or coiled form.

Among the numerous amino acid compositions constituting human hair, cystine is one of the most important amino acids. Cystine is composed of two cysteines (thiols), which are present in different amino acid chains, respectively, and has a disulfide bond known as a very strong bond forming a bond between two sulfur atoms in close proximity to each other. In addition to the disulfide bond, hair includes very abundant peptide bonds. In addition, due to the presence of many CO— and NH— groups, there is hydrogen bonding between neighboring chain molecular groups. However, due to a high cystine content, which is the very unique part of the cell structure of human hair, the physical characteristics of hair are exhibited. A pigment, which is a part related to a hair color, is melanin, and is mainly present in granule form at the cortex of human hair.

Most of the hair consists of a protein, and the other components include the melanin pigment, lipids, trace elements, and water. The protein that constitutes most of the amino acid composition of hair is the keratin protein abundantly containing cysteine. Hair keratin consists of about 18 types of amino acids, and compared to the human epithelium, it has a large cysteine content. In addition, a ratio of basic amino acids, for example, histidine, lysine and arginine is 1:3:10, which is the unique ratio of hair keratin. Skin collagen has high glycine, proline and alanine contents without cysteine. The melanin pigment determining hair color is contained in the hair at about 3% or less.

In addition to the protein and the melanin pigment, it has been known that the hair contains minerals such as copper, zinc, iron, calcium and magnesium, and trace elements, and other than these elements, also contains inorganic components such as phosphorus, silicon, etc.

In addition to the peptide bonds between amino acids in the protein, bonds present in the hair include intermolecular forces or binding strength between molecules of each protein, which maintain the morphology and shape of hair. Types of bonds largely include crosslinking bonds such as a cystine bond and a peptide bond, and non-crosslinking bonds such as an ionic bond, a hydrogen bond and a hydrophobic interaction. Among these, the cystine bond (disulfide bond; —$CH_2$—S—S—$CH_2$—), uniquely formed in a sulfur (S)-containing protein, is a side chain bond not shown in other fibers and a bond characteristically shown in keratin. The cystine bond imparts strong physiochemical characteristics to the keratin.

The keratin protein (58%), which is the main component of hair, consists of amino acids such as glycine, alanine, valine, leucine, isoleucine, threonine, serine, cysteine, cystine, methionine, aspartic acid, asparagine, glutamic acid, diiodotyrosine, lysine, arginine, histidine, phenylalanine, tyrosine, tryptophan, proline and oxyproline, and particularly, the keratin constituting the hair includes about 3.9 to 7.7% of aspartic acid, about 13.6 to 14.2% of glutamic acid, and about 1.9 to 3.1% of lysine.

Generally, fibers may be largely divided into natural fibers and artificial fibers, and among the natural fibers, a fiber obtained from an animal is referred to as an animal fiber, whose chemical component is a protein, and thus is also called a protein-based fiber. The protein-based fibers include a fiber obtained from the coat of an animal and a fiber obtained from cocoons, and the fibers obtained from the animal coat may be divided into wool obtained from the coat of sheep and a hair fiber obtained from goats, camels, rabbits, horses, cows, or other animals.

Like the hair, these protein-based fibers consist of amino acids such as glycine, alanine, valine, leucin, isoleucine, threonine, serine, cysteine, cystine, methionine, aspartic acid, asparagine, glutamic acid, diiodotyrosine, lysine, arginine, histidine, phenylalanine, tyrosine, tryptophan, proline and oxyproline, and the most generally and widely used wool among the protein-based fibers is known to have an amino acid composition similar to the hair.

These protein-based fibers, hair, skin, finger/toe nails and leather are types of very rigid proteins under mild conditions such as water or a neutral solvent, but may be easily damaged by physical/chemical treatment and environmental stress such as combing, heat of a dryer, dyeing or a permanent, which commonly occurs in common life, physical friction in daily life, washing, sunlight, heat of ironing, adsorption of a pollutant, exposure to ultraviolet rays, exposure to high and low temperatures, seawater, or chlorine of a pool. Accordingly, the damaged hair, skin, finger/toe nails, fibers or leather have pores due to the release of proteins inside and outside and thus becomes rough, thereby having problems of decreased softness and elasticity, difficult handling due to increased friction, lower glossiness and a turbid color.

Therefore, to improve the surface characteristics of a substrate such as hair, skin, fibers or leather, and thus maintain beautiful and heathy appearance, a treatment agent is used. Particularly, glossiness, softness and smoothness are important and representative surface characteristics to be improved.

Examples of the treatment agents for imparting strength improvement include hair cosmetic agents, such as a shampoo, a rinse, a treatment, a wax, a spray, a mousse, a hair lotion, a hair cream, a pack, a mask, a sheet, etc., cosmetic agents for skin, such as a skin, a lotion, an essence, a serum, a cream, a gel, a foundation, a powder, a makeup base, point makeup, a mask, a patch, etc., fabric care agents such as a fabric softener, a fabric coloring agent, a detergent, a treatment, a pre/after treatment agent, a laundry aid, a spot stain remover, a spray, etc. The treatment agents also include finger/toe nail treatment agents such as a polisher, a nutrient, an enhancer, etc., and a leather treatment agent such as a cream, a lotion, an essence, a serum, a gel, a wax, a spray, a cleanser, a cleaner, a spot stain remover, a salve-type agent, a polisher, a strip, a sheet, etc.

In addition, generally, the "cosmetic" is used to clean and make the body look more beautiful, enhance attractiveness, change an appearance, or healthily maintain skin or hair by applying, spraying, or other similar methods onto the body, and defined as being slightly effective on the human body. Such cosmetics have various functions for keeping various body parts, such as the skin, hair, and finger/toe nails, healthy and beautiful, and among these functions, strength improvement may be one of the main functions of the cosmetics.

General raw materials constituting the cosmetic for improving strength include oil raw materials such as oil, wax, hydrocarbons, higher fatty acids, higher alcohols, ester oil, silicone oil, etc., anionic, cationic, amphoteric or nonionic surfactants, high-molecular compounds such as moisturizing agents, thickening agents and coating agents, UV absorption/blocking agents, antioxidants, sequestering agents, colorants including dyes and pigments, fragrances, and preservatives.

Other than these materials, as components for exhibiting special performance, oil and natural or synthetic fatty acids, fatty alcohols, alcohols, alkylglycerylethers, esters, hydrocarbons, silicones, fluorine compounds, polyhydric alcohols, saccharides, natural or synthetic polymers, wax, vitamins, hormones, amino acids, peptides, proteins, animal/plant extracts, mineral extracts, and derivatives thereof may be included.

However, most of the components for improving strength included in this composition impart their effect through simple adsorption, rather than strong covalent bonding. Due to the various external environments that are experienced in daily lives after the treatment of the composition, these components are continuously released, and strength is gradually lowered, and during a cleansing process, such a phenomenon is further accelerated.

For example, in Korean Unexamined Patent Application Publication No. 2014-0096053, a method for glossy makeup through coating with a keratin substance (particularly, for nails) including an alkoxy silane and water contained at a predetermined molar ratio obtained using a specific equation, and a related kit composition are disclosed. However, due to the limitation in that only one part of the silane molecule is bound to the protein surface through dehydration, the composition has a coating ability, but is not effective in strength improvement which can be obtained by binding between the silane molecule and the protein at both ends.

DISCLOSURE

Technical Problem

The present invention is directed to providing a composition for enhancing protein strength, which is effective in semi-permanent improvement in the strength of hair, scalp, skin, finger/toe nails, leather or fiber.

The present invention is also directed to providing a care product including the composition for enhancing protein strength.

Technical Solution

To solve the problems of the present invention, the present invention provides a composition for enhancing protein strength, which includes an aminosilane compound and a reaction mediator.

In addition, the present invention provides a care product including the composition.

Advantageous Effects

A composition for enhancing protein strength according to the present invention contains an aminosilane compound which enables covalent bonding with a protein of hair, scalp, skin, finger/toe nails, leather or fiber, thereby forming a covalent bond between the protein and an aminosilane compound, and thus a protein strength enhancing effect may be improved, and a semi-permanent protein strength enhancing effect can be maximized.

MODES OF THE INVENTION

The present invention relates to a composition for enhancing protein strength, which includes an aminosilane compound and a reaction mediator.

The "composition for enhancing protein strength" used herein refers to a composition acting to semi-permanently link proteins through covalent bonding between an aminosilane compound and carboxyl groups and amine groups, which are present in large amounts as a constituent component of a hair, scalp, finger/toe nail, skin or fiber protein, to enhance protein strength. In addition, the composition for enhancing protein strength refers to a composition which makes a protein appear thicker, and has side effects such as increasing elasticity and thickness.

The "composition for enhancing protein strength" may include a composition for enhancing the strength of a hair protein, a composition for enhancing the strength of a scalp protein, a composition for enhancing the strength of a skin protein, a composition for enhancing the strength of a finger/toe nail protein, a composition for enhancing the strength of a leather protein and/or a composition for enhancing the strength of a fiber protein.

The composition for enhancing protein strength according to the present invention may allow a reaction between a substrate consisting of a protein and an aminosilane compound using a reaction mediator to form a covalent bond between a carboxyl group of the protein substrate and an amine group of the aminosilane compound, between an amine group of the protein substrate and a carboxyl group of the aminosilane compound and/or between the amine group of the protein substrate and an amine group of the aminosilane compound, and thus a protein strength enhancement effect may be semi-permanently maximized.

The "substrate consisting of a protein" includes, for example, hair, scalp, skin, finger/toe nails, leather and fiber, but the present invention is not limited thereto.

The "aminosilane compound" used herein includes mono-, di- and tri-alkoxyaminosilane compounds represented by the following Formulas 1 to 3, which have at least one or more amine groups in the same molecule as well as forming one to three hydroxyl groups directly binding to silicon (Si) by hydrolysis with water.

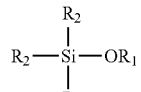

[Formula 1]

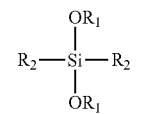

[Formula 2]

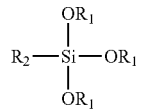

[Formula 3]

In Formulas 1 to 3, $R_1$ is each independently hydrogen; or a linear, branched or cyclic hydrocarbon having 1 to 500 carbon atoms or a benzene ring hydrocarbon, which includes one or more double bonds in a part of the molecule, or is substituted with one or more atoms selected from the group consisting of O, N, S, P and Si or substituted in an anionic, cationic or amphoteric form, or includes a structure to which a metal ion is bonded in a salt form; and $R_2$ is each independently a linear, branched or cyclic hydrocarbon having 1 to 500 carbon atoms or a benzene ring hydrocarbon, which includes one or more double bonds in a part of the molecule, or is substituted with one or more atoms selected from the group consisting of O, N, S, P and Si or substituted in an anionic, cationic or amphoteric form, or includes a structure to which a metal ion is bonded in a salt form and in which at least one primary or secondary amine is included at an end of the molecular structure.

The aminosilane compound may be one or more selected from the group consisting of 3-aminopropyltriethoxysilane, bis[(3-triethoxysilyl)propyl]amine, 3-aminopropyltrimethoxysilane, 4-aminobutyltriethoxysilane, bis[(3-trimethoxyslyl)propyl]amine, 3-aminopropylmethyldiethoxysilane, 3-aminopropyldimethylethoxysilane, 3-aminopropylmethyldimethoxysilane, aminoethylaminopropyltrimethoxysilane, aminoethylaminopropyltriethoxysilane, aminoethylaminopropylmethyldimethoxysilane, diethylenetriaminopropylmethyldimethoxysilane, piperazinylpropylmethyldimethoxysilane, (n-phenylamino)methyltrimethoxysilane, (n-phenylamino)methyltriethoxysilane, 3-(n-phenylamino)propyltrimethoxysilane, n-(n-butyl)-3-aminopropyltrimethoxysilane, 4-aminobutyltriethoxysilane, m-aminophenyltrimethoxysilane, p-aminophenyltrimethoxysilane, aminophenyltrimethoxysilane, m-aminophenyltriethoxysilane, p-aminophenyltriethoxysilane, aminophenyltriethoxysilane, 3-aminopropyltris(methoxyethoxy-ethoxy)silane, 11-aminoundecyltriethoxysilane, 3-(m-aminophenoxy(propyltrimethoxy-silane), aminopropylsilanetriol, 3-aminopropylmethyldiethoxysilane, 3-aminopropyldiisopropylethoxysilane, 3-aminopropyldimethylethoxysilane, n-(2-aminoethyl)-3-aminopropyltri-methoxysilane, n-(2-aminoethyl)-3-aminopropyltri-ethoxysilane, n-(6-aminohexyl)aminomethyl-triethoxysilane, n-(6-aminohexyl)aminopropyl-trimethoxysilane, n-(2-aminoethyl)-11-aminoundecyl-trimethoxysilane, (aminoethylaminomethyl)phenethyl-trimethoxysilane, n-3-[(amino(polypropylenoxy)]amino-propyltrimethoxysilane, n-(2-aminoethyl)-3-aminopropyl-silanetriol, n-(2-aminoethyl)-3-aminopropylmethyl-dimethoxysilane, n-(2-aminoethyl)-3-aminoisobutyl-methyldimethoxysilane, (aminoethylamino)-3-isobutyldi-methylmethoxysilane, (3-trimethoxysilylpropyl)diethylene-triamine, n-butylaminopropyltrimethoxy-silane, n-ethylaminoisobutyltrimethoxy-silane, n-methylaminopropyltrimethoxy-silane, n-phenylaminopropyltrimethoxy-silane, 3-(n-allylamino)propyltrimethoxy-silane, (cyclohexylaminomethyl)triethoxysilane, n-cyclohexylaminopropyltrimeth-oxysilane, n-ethylaminoisobutylmethyl-diethoxysilane, (phenylaminomethyl)methyl-dimethoxysilane, n-phenylaminomethyltriethoxysilane, n-methylaminopropylmethyl-dimethoxysilane, 3-(n-styrylmethyl-2-aminoethylamino)-propyltrimethoxysilane hydrochloride, n-(trimethoxysilylpropyl)isothio-uronium chloride, bis[(3-trimethoxysilyl)propyl]-ethylenediamine, bis[(3-trimethoxysilyl)propyl]-ethylenediamine, bis[3-(triethoxysilyl)propyl]urea, bis(trimethoxysilylpropyl)urea, bis(methyldiethoxysilylpropyl)amine, ureidopropyltriethoxysilane, acetamidopropyltrimethoxysilane, n-[5-(trimethoxysilyl)-2-aza-1-oxo-pentyl]caprolactam and ureidopropyltrimethoxysilane, but the present invention is not limited thereto.

The aminosilane compound may be contained at 0.000001 to 30 parts by weight, 0.001 to 15 parts by weight, 0.01 to 5 parts by weight with respect to 100 parts by weight of the total composition. When the content of the aminosilane compound is less than 0.000001 part by weight, it is difficult to exhibit an effect of continuously enhancing protein strength, and when the content of the aminosilane compound is more than 30 parts by weight, an amine present in the aminosilane compound is contained in the composition at an excessively large amount, so that there may be a problem with stability of a formulation.

In the present invention, the reaction mediator includes one or more selected from the group consisting of a carbodiimide-based compound, a dihydroxyquinoline-based compound, an aminium-based compound, a phosphonium-based compound and an enzyme.

The carbodiimide-based compound is a compound having at least one methane diimine (—N=C=N—) in the molecule, and may include a component represented by Formula 4 below:

[Formula 4]

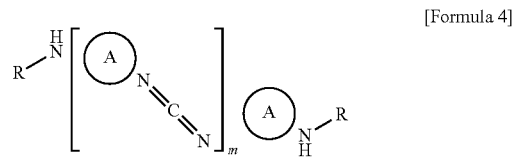

In Formula 4, A each independently represents a monomer selected from structures listed below,

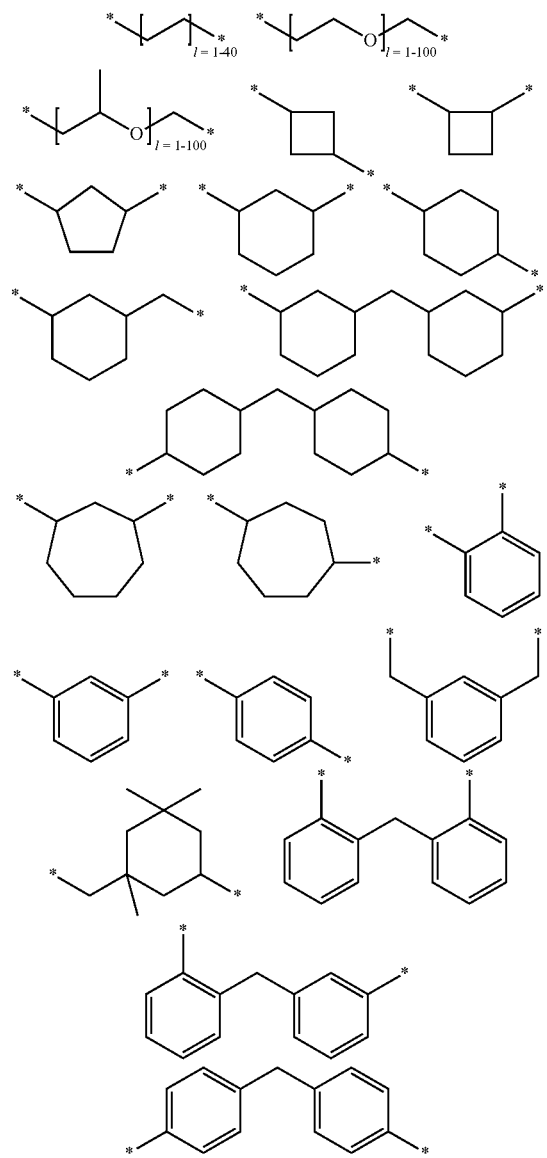

wherein * denotes a connecting position,

R represents each independently hydrogen; or C1 to C500 linear, branched or cyclic hydrocarbon; or an aromatic hydrocarbon, wherein a portion of the linear, branched, cyclic or aromatic hydrocarbon molecule includes a double bonds, is substituted with one or more atoms selected from the group consisting of O, N, S, P and Si, and m is an integer of 1 to 100, and when m is 2 or greater, each of

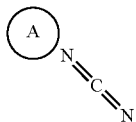

is the same or different from each other.

The carbodiimide-based compound may be one or more selected from the group consisting of 1,1'-methylene-bis-(4-isocyanatocyclohexane)-, homopolymer, polyethylene glycol mono-Me-ether-blocked; 1,1'-methylene-bis-(3-isocyanatocyclohexane)-, homopolymer, polyethylene glycol mono-Me-ether-blocked; 1,1'-methylene-bis-(4-isocyanatocycloheptane)-, homopolymer, polyethylene glycol mono-Me-ether-blocked; 1,1'-methylene-bis-(3-isocyanatocycloheptane)-, homopolymer, polyethylene glycol mono-Me-ether-blocked; 1,1'-methylene-bis-(3-isocyanatocyclopentane)-, homopolymer, polyethylene glycol mono-Me-ether-blocked; benzene; 1,3-bis(1-isocyanato-1-methylethyl)-, homopolymer, polyethylene glycol mono-Me-ether-blocked; 1-ethyl-3-(3-dimethylaminopropyl)carbodiimide; and 1-ethyl-3-(3-dimethylaminopropyl)carbodiimide HCl, but the present invention is not limited thereto.

In one exemplary embodiment, as a reaction mediator, a carbodiimide-based compound such as benzene; 1,3-bis(1-isocyanato-1-methylethyl)-, homopolymer, polyethylene glycol mono-Me-ether-blocked; or 1,1'-methylene-bis-(4-isocyanatocyclohexane)-, homopolymer, polyethylene glycol mono-Me-ether-blocked may be used.

The dihydroxyquinoline-based compound may be a compound represented by Formula 5 below:

[Formula 5]

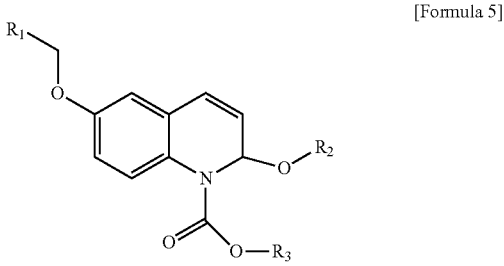

In Formula 5, $R_1$ may be one selected from the group consisting of aqueous non-ionic polymers; bead- and resin-type polymer resins; and silica beads, and $R_2$ and $R_3$ may be each independently a linear or branched saturated alkyl group having 1 to 10 carbon atoms; or an unsaturated alkyl group.

The aqueous non-ionic polymer may be one or more polymers selected from the group consisting of polyethylene glycol (PEG), polyvinyl alcohol (PVA), polyethylene oxide (PEO), polyacrylonitrile (PAN), polyvinylpyrrolidone (PVP), polyisopropylacrylamide (PNIPPAm), a cellulose derivative, a starch derivative, dextran and guar gum, each having a molecular weight of less than 20,000 Da, but the present invention is not limited thereto. When the molecular weight of the aqueous non-ionic polymer is 20,000 Da or more, a proportion of the dihydroxyquinoline-based compound inducing covalent bonding is too small, it is difficult to exhibit a glossy effect.

The bead- and resin-type polymer resin may be a polymer prepared by polymerizing one or more monomers selected from the group consisting of styrene, ethylene, butadiene, acrylonitrile, methylstyrene, terephthalate, ethylene chloride, ketone ether, imide ether, sulfone ether, phthalamide, phenylene ether, phenylene oxide, phenylsulfide, sulfone, urethane, vinylidene fluoride and tetrafluoroethylene, each having a molecular weight of less than 20,000 Da, but the present invention is not limited thereto.

When the molecular weight of the bead- and resin-type polymer resins is more than 20,000 Da, a proportion of the dihydroxyquinoline-based compound inducing covalent bonding is very small, it is difficult to exhibit a glossy effect.

The silica bead may have a diameter of 100 nm to 1 mm, for example, 100 nm to 100 µm, 1 to 100 µm, or 1 to 70 µm. When the diameter of the silica bead is smaller than 100 nm, there may be a problem with safety on the skin surface, and when the diameter of the silica bead is larger than 1 mm, there are problems with formulation and stabilization.

The reaction mediator of the present invention may be an aminium-based compound, which is a cationic compound having a $—R_3NH^+$ structure formed by the hydrogenation of one amine; or a phosphonium salt $(PH_4^+)$ series compound having a $PH_4^+$ structure as a polyatomic cation, but the present invention is not limited thereto. $R_3$ is hydrogen; or a linear, branched or cyclic hydrocarbon having 1 to 500 carbon atoms or a benzene ring hydrocarbon, which includes one or more double bonds in a part of the molecule, or is substituted with one or more atoms selected from the group consisting of O, N, S, P and Si or substituted in an anionic, cationic or amphoteric form, or includes a structure to which a metal ion is bonded in a salt form.

The aminium-based compound may be one or more selected from the group consisting of N-[(1H-benzotriazol-1-yl)(dimethylamino)methylene]-N-methylmethanaminium hexafluorophosphate N-oxide, N-[(1H-benzotriazol-1-yl)(dimethylamino)methylene]-N-methylmethanaminium hexafluoroborate, 2-(3,4-(N-[(1H-benzotriazol-1-yl)(dimethylamino)methylene]-N-methylmethanaminium hexafluorophosphate N-oxide, 2-(3,4-dihydro-4-oxo-1,2,3-benzotriazin-3-yl)-1,1,3,3,-tetramethyl uronium tetrafluoroborate, O-(3,4,-dihydro-4-oxo-5-azabenzo-1,2,3-triazin-3-yl)-1,1,3,3,-tetramethyluronium hexafluoroborate, O-(3,4,-dihydro-4-oxo-5-azabenzo-1,2,3-triazin-3-yl)-1,1,3,3,-tetramethyluronium hexafluorophosphate, 2-(2-oxo-1(2H)-pyridyl-1,1,3,3,-tetramethyluronium tetrafluoroborate, 2-(2-oxo-1(2H)-pyridyl-1,1,3,3-tetramethyluronium tetrafluorophosphate, 2-succinimido-1,1,3,3-tetramethyluronium tetrafluoroborate), 2-succinimido-1,1,3,3-tetramethyluronium tetrafluorophosphate, N,N,N',N'-bis(tetramethylene-O-pentafluorophenyluronium tetrafluoroborate, N,N,N',N'-bis(tetramethylene-O-pentafluorophenyluronium hexafluorophosphate, N—[6-trifluoromethyl(1H-benzotriazol-1-yl)(dimethylamino)methylene]-N-methyl methanaminium tetrafluoroborate N-oxide, N—[6-trifluoromethyl(1H-benzotriazol-1-yl)(dimethylamino)methylene]-N-methylmethanaminium hexafluorophosphate N-oxide, N—[(dimethylamino)-1H-1,2,3-triazolo[4,5,b]pyridin-1-yl]methylene]-N-methylmethanaminium hexafluorophosphate N-oxide, N—[(dimethylamino)-1H-1,2,3-triazolo[4,5-b]pyridin-1-ylmethylene]-N-methyl methanaminium tetrafluoroborate N-oxide, N—[(dimethylamino)-1H-1,2,3-triazolo[4,5-b]pyridin-1-ylmethylene]-N-methylmethanaminium hexafluorophosphate N-sulfide, S-(1-oxido-1-pyridinyl)-1,1,3,3-tetramethylthiouronium hexafluorophosphate, 0-[cyano(ethoxycarbonyl)methyleneamino]-N,N,N',N'-tetramethyluronium tetrafluoroborate, O-[cyano(ethoxycarbonyl) methylene amino]-N,N,N',N'-tetramethyluronium hexafluorophosphate, O-[(dicyano methylidene)-amino]-1,1,3,3-tetramethyluronium hexafluorophosphate, O-[(dimethoxycarbonylmethylidene)-amino]-1,1,3,3-tetramethyluronium hexafluorophosphate, N—[(cyano(pyridin-2-yl)methylene aminooxy) (dimethylamino)methylene]-N-methylmethanaminium hexafluorophosphate, 2-(5-norbornene-2,3-dicarboximido)-1,1,3,3-tetramethyluronium tetrafluoroborate, 2-phthalimido-1,1,3,3-tetramethyluronium tetrafluoroborate, bis(tetra methylene) chloroformamidinium hexafluorophosphate, (1H-benzotriazol-1-yl)(1-pyrollidinylmethylene) pyrrolidinium hexafluorophosphate N-oxide, 1-(1-pyrrolidinyl-1H-1,2,3-triazolo[4,5-b]pyridin-1-ylmethylene) pyrrolidinium hexafluorophosphate N-oxide, O-(3,4-dihydro-4-oxo-1,2,3-benzo triazin-3-yl)-1,1,3,3-bis(tetramethylene)uranium hexafluorophosphate, O-(3,4-dihydro-4-oxo-5-azabenzo-1,2,3-triazin-3-yl)-1,1,3,3-bis(tetramethylene) uranium hexafluorophosphate, N,N,N',N'-bis(tetra methylene)-O-pentafluoro phenyluronium hexafluorphosphate, N,N,N',N'-bis(tetramethylene)-S-pentafluorothiophenyluronium hexafluorphosphate, 1-(1-pyrrolidinyl-1H-1,2,3-triazolo[4,5-b]pyridin-1-ylmethylene) pyrrolidinium hexafluorophosphate N-sulfide, N,N,N',N'-bis(tetramethylene)-O-2-nitrophenyluronium hexafluorophosphate, N,N,N',N'-bis(tetramethylene)-O-pentafluorophenyluronium hexafluorohosphate, O-(benzotriazol-1-yl)-1,1,3,3-bis(pentamethylene) hexafluorophosphate, O-(7-azabenzotriazol-1-yl)-1,1,3,3-bis(pentamethylene)-uronium hexafluorophosphate, 2-[2-oxo-1(2H)-pyridyl]-1,1,3,3-bis(pentamethylene) uronium tetrafluoroborate, 2-chloro-1,3-dimethylimidazolidinium hexafluorophosphate, O-(benzotriazol-1-yl)-1,3-dimethyl-1,3-dimethylene uronium hexafluorophosphate, O-(7-azabenzotriazol-1-yl)-1,3-dimethyl-1,3-dimethyleneuronium hexafluorophosphate, 2-chloro-1,3-dimethylpyrimidinium hexafluorophosphate, O-(benzotriazol-1-yl)-1,3-dimethyl-1,3-trimethyleneuronium hexafluorophosphate, O-(7-azabenzotriazol-1-yl)-1,3-dimethyl-1,3-trimethyleneuronium hexafluorophosphate, (7-benzotriazol-yl)-1,1,3-tri methyl-1-hexafluorophosphate, (7-azabenzotriazol-yl)-1,1,3-trimethyl-1-phenyluronium hexafluorophosphate, O-(1H-benzotriazol-1-yl)-1,1-dimethyl-3,3-tetramethylene uranium hexafluorophosphate, O-(1H-1,2,3-triazolo[4,5-b]pyridin-yl)-1,1-dimethyl-3,3-tetramethyleneuronium hexafluorophosphate, O-(1H-benzotriazol-1-yl)-1,1-dimethyl-3,3-pentamethylene uranium hexafluorophosphate, 6-chloro-1((dimethylamino)(morpholino)methylene)-1H-benzo triazolium hexafluorophosphate-3 oxide, 3-((dimethylamino)-(morpholino)methylene)-1H-[1,2,3]triazolo[4,5-b]pyridinium hexafluorophosphate, 6-trifluoromethyl-1-((dimethylamino)-(morpholino)methylene)-1H-benzotriazoliumhexafluorophosphate-3-oxide, 1-((dimethylamino)-(morpholino)) oxypentafluorophenyl-metheniminium hexafluorophosphate, 1-[(1-(cyano-2-ethoxy-2-oxoethylideneaminooxy)-dimethylamino morpholinomethylene)]methanaminium hexafluorophosphate, 1-[(1-(dicyanomethyleneaminooxy) dimethylamino morpholinomethylene)] methanaminium hexafluorophosphate, 1-[(1,3-diethoxy-1,3-dioxopropan-2-ylideneaminooxy) dimethylaminomorpholinomethylene)]methanaminium hexafluorophosphate, N—[(cyano(pyridin-2-yl)methyleneaminooxy) (dimethylamino)methylene]-N-morpholinomethanaminiumhexafluorophosphate, 1-[(1-(cyano-2-ethoxy-2-oxoethylideneaminooxy) dimethylaminopyrrolodino methylene)]methanaminium hexafluorophosphate, 1-((dicyanomethyleneaminooxy) morpholinomethylene)pyrrolidinium hexafluorophosphate, 1-[(1,3-diethoxy-1,3-dioxopropan-2-yldeneaminooxy)-dimethylamino-pyrrolodinomethylene]]methanaminium hexafluorophosphate, 1-[(1-(cyano-2-ethoxy-2-oxoethylidene aminooxy)-dimethylamino-pyrrolodinomethylene)] methanaminium hexafluororphosphate, 1-((1-cyano-2-ethoxy-2-oxoethylideneaminooxy)(morpholino) methylene) pyrrolidinium hexafluorophosphate, benzotriazol-1-yloxy-N,N-dimethyl-methanaminium hexachloroantimonate, 5-(1H-benzotriazol-1-yloxy)-3,4-dihydro-1-methyl-2H-pyrrolium hexachloroantimonate, 5-(7-azabenzotriazol-1-yloxy)-3,4-dihydro-1-methyl-2H-pyrrolium hexachloroantimonate, 1-(1H-benzotriaol-1-yloxy)phenyl-methylene pyrrolidinium hexachloroantimonate, 5-(pentafluorophenyloxy)-3,4-dihydro-1-methyl-2H-pyrrolium hexachloroantimonite, 5-(succinimidyloxy)-3,4-dihydro-1-methyl-2H-pyrrolium hexachloroantimonate, 5-(3',4'-dihydro-4'-oxo-1',2',3'-benzotriazin-3'-yloxy)-3,4-diydro-1-methyl-2H-pyrrolium hexachloroantimonate) and a derivative thereof, but the present invention is not limited thereto.

The phosphonium-based compound may be one or more selected from the group consisting of benzotriazol-1-yloxy-tris(dimethylamino) phosphonium hexafluorophosphate, bromotris (dimethylamino) phosphonium hexafluorophosphate, chlorotri (pyrrolidino) phosphonium hexafluorophosphate, bromotri (pyrrolidino) phosphonium hexafluorophosphate, chloro-tris(dimethylamino) phosphonium hexafluorophosphate, benzotriazol-1-yloxytri (pyrrolidino) phosphonium hexafluorophosphate, [(7-azabenzotriazol-1-yl)oxy]tris-(dimethylamino) phosphonium hexafluorophosphate, [(7-azabenzotriazol-1-yl)oxy]tris-(pyrrolidino) phosphonium hexaflurophosphate, 0-[(cyano-(ethoxycarbonyl)methyliden)-amino]-yloxytripyrrolidino phosphonium hexafluorophosphate, [(6-nitrobenzotriazol-yl)oxy]tris-(pyrrolidino) phosphonium hexafluorophosphate, [(6-trifluoromethyl)benzotriazol-1-yl]oxy-tris(pyrrolidino)phosphonium hexafluorophosphate, [4-nitro-6-(trifluoromethyl) benzotriazol-1-yl]oxy]tris(pyrrolidino) phosphonium hexafluorophosphate, (6-chloro-benzotriazol-1-yloxy)tris (pyrrolidino)-phosphonium hexafluorophosphate, N',N',N',N'-bis(tetramethylene)-O-pentafluoro phenyluronium hexafluorophosphate, (pyridyl-2-thio)tris (pyrrolidino)-phosphonium hexafluorophosphate, [(3,4-dihydro-4-oxo-1,2,3-benzotriazin-3-yl)oxy]tris-(pyrrolidino)phosphonium hexafluorophosphate, [(3,4-dihydro-4-oxo-5-azabenzo-1,2,3-triazin-3-yl] tris-(pyrrolidino) phosphonium hexafluorophosphate and a derivative thereof, but the present invention is not limited thereto.

The enzyme may be transglutaminase, sortase A, tyrosinase, laccase/peroxidase or lysyl oxidase/amine oxidase, which mediates bioconjugation between the amine of glutamine and the amine of lysine, but the present invention is not limited thereto.

The reaction mediator may be used at 0.000001 to 10 parts by weight, 0.001 to 7 parts by weight, or 0.01 to 5 parts by weight with respect to 100 parts by weight of the total composition. When the content of the reaction mediator is less than 0.000001 part by weight, it is difficult to exhibit a continuous surface improvement effect, and when the content of the reaction mediator is more than 10 parts by weight, the reaction mediator excessively present in an amount higher than a reaction position present in a substrate consisting of a protein reacts with a functional component while not reacting with the protein substrate, and thus it does not help to improve the sustainability of glossiness, and is rather lost.

This reaction may be performed under a condition of pH 2 to pH 12, and more preferably, at pH 3 to pH 10, and most preferably, in a weakly acidic aqueous solution of pH 4.5 to pH 8 to maximize reaction efficiency. The reaction is finished within 1 minute to 30 minutes.

The composition may be used by coating, spraying, dilution, or other similar methods, and dehydration may be promoted under a mild condition such as an elevated temperature (20 to 80° C.) at which thermal denaturation of a protein does not occur, and thus the reaction efficiency may be enhanced.

In one exemplary embodiment, using a carbodiimide-based compound as a reaction mediator, a reaction between a carboxyl group on the surface of the substrate consisting of a protein and an amine group of triethoxyaminopropylsilane is illustrated in Reaction Scheme 1 below.

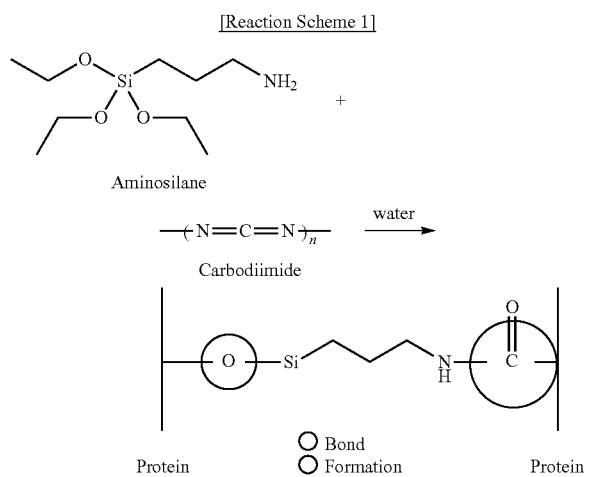

As shown in Reaction Scheme 1, an amino acid linked to hair, scalp, skin, finger/toe nails, leather and/or fiber is not easily detached in general cleansing with a shampoo, a detergent or a soap, and thus the structure attached to the hair, scalp, skin, finger/toe nails, leather and/or fiber may be almost permanently maintained.

The composition for enhancing protein strength according to the present invention may further include a component capable of improving a protein strength enhancement effect, other than the aminosilane compound and the reaction mediator. For example, the composition may be easily prepared when mixed with a fatty acid such as palmitic acid, stearic acid, lauric acid or myristic acid, a cationic surfactant such as a fatty alcohol, or a linear or branched long-chain alkyl quaternary ammonium salt, a cationic polymer such as cationic cellulose, cationic guar gum or cationic polyvinylpyrrolidone, or silicone. In addition, for formulation as a cosmetic preparation, components for preparing a cosmetic such as a solvent, a surfactant, a thickening agent, a stabilizer, a preservative, a coloring agent, a pH adjustor, a sequestering agent, a coloring agent, a pearlizing agent, an appearance improving agent, a pigment and powder particles may be further included. The components for preparation may be used at 40 to 99 parts by weight with respect to 100 parts by weight of the total composition.

The composition for enhancing protein strength according to the present invention may include an aminosilane compound with a functional group and thus is able to be used in the formulation of a composition for enhancing protein strength. Examples of the composition for hair may include all cosmetic preparations capable of being used for hair, for example, a pre-shampoo product, a shampoo, a rinse, a treatment, a wax, a spray, a mousse, a hair lotion, an essence, a hair cream, a pack, a mask, a tablet, a patch, a strip, a slave, a permanent hair dye, a temporary hair dye and a hair waving agent, examples of the composition for skin may include all cosmetic preparations capable of being used for skin, for example, a skin toner, a lotion, an essence, a serum, a cream, a gel, a foundation, a powder, a makeup base, a point makeup product, a mask and a patch, examples of the composition for fabric may include all fabric care preparations capable of being used in fabric, for example, a fabric softener, a fabric dye, a washing detergent, a treatment, a pre/after care agent, a laundry supplement, a spot stain remover and a spray. Examples of the composition for leather may include all preparations for treating leather, for example, a cream, a lotion, an essence, a serum, a gel, a wax, a spray, a cleanser, a cleaner, a spot stain remover, a salve, a temporary dye, a permanent dye, a polish, a stripping agent and a sheet, but the present invention is not limited thereto.

To enhance the protein strength enhancement effect in the composition for enhancing protein strength according to the present invention, a di-basic acid ester oil such as dioctyl succinate, dioctyl adipate or diethyl sebacate, polyol, polyethylene glycol, propylene glycol, hexylene glycol, butanediol and their isomers, and glycerol, benzyl alcohol, ethoxydiglycol and their derivatives may be used. The above-mentioned solvents increase the permeability of hair and skin and are used as solvents for a poorly soluble substance.

The advantages and features of the present invention, and methods of attaining the same will be clarified with reference to examples that will be described below in detail. However, the present invention may be embodied in a variety of different forms and is not limited to the examples described below, and the examples are merely provided to complete the disclosure of the present invention, and fully inform the scope of the present invention to those of ordinary skill in the art.

Examples 1 to 12 and Comparative Examples 1 to 4

Shampoo compositions for enhancing the strength of a hair protein according to Examples 1 to 12 and Comparative Examples 1 to 4 were prepared with compositions and contents shown in Tables 1 and 2 below. Hair was thoroughly washed with each of the prepared shampoo compositions, and then about 3 g of a towel-dried hair tress was prepared, and therefrom, 50 strings of the hair were randomly extracted to measure a tensile strength using a hair tensile strength tester, and the result was determined to be hair tensile strength before use of the composition. Shampooing was performed 30 times on the specimens prepared from the same tress using 0.3 g of each composition, and then subjected to the measurement of tensile strength to evaluate strength variations. The results obtained from the all compositions were compared.

TABLE 1

| (Parts by weight) | Example 1 | Example 2 | Example 3 | Example 4 | Example 5 | Example 6 |
|---|---|---|---|---|---|---|
| Water | To 100 | To 100 | To 100 | To 100 | To 100 | To 100 |
| Polyquaternium-10 | 0.5 | 0.5 | 0.5 | 0.5 | 0.5 | 0.5 |
| EDTA 4Na | 0.05 | 0.05 | 0.05 | 0.05 | 0.05 | 0.05 |
| Sodium Lauryl Ether(2 mole) Sulfate (30%) | 35 | 35 | 35 | 35 | 35 | 35 |
| Cocamidopropyl Betaine (30%) | 15 | 15 | 15 | 15 | 15 | 15 |
| Fragrance | 0.9 | 0.9 | 0.9 | 0.9 | 0.9 | 0.9 |
| 3-aminopropyltriethoxysilane | 0.5 | — | — | — | 0.5 | — |
| 3-aminopropylmethyldiethoxysilane | — | 0.5 | — | — | — | 0.5 |
| 3-aminopropyldimethylethoxysilane | — | — | 0.5 | — | — | — |
| p-aminophenyltriethoxysilane | — | — | — | 0.5 | — | — |
| Benzene,1,3-bis(1-isocyanato-1-methylethyl)-, homopolymer, polyethylene glycol mono-Me-ether-blocked | 1 | 1 | 1 | 1 | — | — |
| 1,1'-methylene-bis-(4-isocyanatocyclohexane)-, homopolymer, polyethylene glycol mono-Me-ether-blocked | — | — | — | — | 1 | 1 |
| N-[(1H-benzotriazole-1-yl)(dimethylamino)methylene]-N-methylmethaneaminium hexafluorophosphate N-oxide | — | — | — | — | — | — |
| Benzotriazole-1-yloxytris(dimethylamino)phosphonium hexafluorophosphate | — | — | — | — | — | — |
| pH adjustor | q.s. | q.s. | q.s. | q.s. | q.s. | q.s. |
| Total | 100 | 100 | 100 | 100 | 100 | 100 |

| (Parts by weight) | Example 7 | Example 8 | Example 9 | Example 10 | Example 11 | Example 12 |
|---|---|---|---|---|---|---|
| Water | To 100 | To 100 | To 100 | To 100 | To 100 | To 100 |
| Polyquaternium-10 | 0.5 | 0.5 | 0.5 | 0.5 | 0.5 | 0.5 |
| EDTA 4Na | 0.05 | 0.05 | 0.05 | 0.05 | 0.05 | 0.05 |
| Sodium Lauryl Ether(2 mole) Sulfate (30%) | 35 | 35 | 35 | 35 | 35 | 35 |
| Cocamidopropyl Betaine (30%) | 15 | 15 | 15 | 15 | 15 | 15 |
| Fragrance | 0.9 | 0.9 | 0.9 | 0.9 | 0.9 | 0.9 |
| 3-aminopropyltriethoxysilane | — | — | 0.2 | 0.2 | 0.5 | 0.5 |
| 3-aminopropylmethyldiethoxysilane | — | — | 0.2 | 0.2 | — | — |
| 3-aminopropyldimethylethoxysilane | 0.5 | — | 0.2 | 0.2 | — | — |
| p-aminophenyltriethoxysilane | — | 0.5 | 0.2 | 0.2 | — | — |
| Benzene,1,3-bis(1-isocyanato-1-methylethyl)-, homopolymer, polyethylene glycol mono-Me-ether-blocked | — | — | — | 0.5 | — | — |
| 1,1'-methylene-bis-(4-isocyanatocyclohexane)-, homopolymer, polyethylene glycol mono-Me-ether-blocked | 1 | 1 | 1 | 0.5 | — | — |

TABLE 1-continued

| | | | | | | |
|---|---|---|---|---|---|---|
| N-[(1H-benzotriazole-1-yl)(dimethylamino)methylene]-N-methylmethaneaminium hexafluorophosphate N-oxide | — | — | — | — | 1 | — |
| Benzotriazole-1-yloxytris(dimethylamino) phosphonium hexafluorophosphate | — | — | — | — | — | 1 |
| pH adjustor | q.s. | q.s. | q.s. | q.s. | q.s. | q.s. |
| Total | 100 | 100 | 100 | 100 | 100 | 100 |

TABLE 2

| (Parts by weight) | Comparative Example 1 | Comparative Example 2 | Comparative Example 3 | Comparative Example 4 |
|---|---|---|---|---|
| Water | To 100 | To 100 | To 100 | To 100 |
| Polyquaternium-10 | 0.5 | 0.5 | 0.5 | 0.5 |
| EDTA 4Na | 0.05 | 0.05 | 0.05 | 0.05 |
| Sodium Lauryl Ether(2 mole) Sulfate (30%) | 35 | 35 | 35 | 35 |
| Cocamidopropyl Betaine (30%) | 15 | 15 | 15 | 15 |
| Fragrance | 0.9 | 0.9 | 0.9 | 0.9 |
| 3-aminopropyl triethoxysilane | 0.5 | — | — | — |
| 3-aminopropylmethyldiethoxysilane | — | 0.5 | — | — |
| 3-aminopropyldimethylethoxysilane | — | — | 0.5 | — |
| p-aminophenyltriethoxysilane | — | — | — | 0.5 |
| Benzene, 1,3-bis(1-isocyanato-1-methylethyl)-, homopolymer, polyethylene glycol mono-Me-ether-blocked | — | — | — | — |
| 1,1'-methylene-bis-(4-isocyanatocyclohexane)-, homopolymer, polyethylene glycol mono-Me-ether-blocked | — | — | — | — |
| N-[(1H-benzotriazole-1-yl)(dimethylamino)methylene]-N-methylmethaneaminium hexafluorophosphate N-oxide | — | — | — | — |
| Benzotriazole-1-yloxytris(dimethylamino) phosphonium hexafluorophosphate | — | — | — | — |
| pH adjustor | q.s. | q.s. | q.s. | q.s. |
| Total | 100 | 100 | 100 | 100 |

TABLE 3

|  | Example 1 | Example 2 | Example 3 | Example 4 | Example 5 | Example 6 |
|---|---|---|---|---|---|---|
| Tensile strength increase rate (%) | 56.3 | 55.2 | 53.3 | 52.9 | 76.3 | 75.2 |

|  | Example 7 | Example 8 | Example 9 | Example 10 | Example 11 | Example 12 |
|---|---|---|---|---|---|---|
| Tensile strength increase rate (%) | 73.4 | 73 | 75.8 | 76.9 | 55.2 | 53.1 |

TABLE 4

|  | Comparative Example 1 | Comparative Example 2 | Comparative Example 3 | Comparative Example 4 |
|---|---|---|---|---|
| Tensile strength Increase rate (%) | 31.6 | 28.3 | 25.6 | 20.3 |

As shown in Tables 3 and 4, the experiments for the compositions of Examples 1 to 12 and Comparative Examples 1 to 4 showed that, compared to the compositions of Comparative Examples 1 to 4 including only an aminosilane component without a reaction mediator, the compositions including, as a reaction mediator, benzene, 1,3-bis(1-isocyanato-1-methylethyl)-, homopolymer, polyethylene glycol mono-Me-ether-blocked (Examples 1 to 4 and 10) or 1,1'-methylene-bis-(4-isocyanatocyclohexane)-, homopolymer, polyethylene glycol mono-Me-ether-blocked (Examples 5 to 10), N-[(1H-benzotriazole-1-yl)(dimethylamino)methylene]-N-methylmethaneaminium hexafluorophosphate N-oxide (Example 11) and benzotriazole-1-yloxytris(dimethylamino)phosphonium hexafluorophosphate (Example 12) exhibit a very excellent hair tensile strength enhancement effect after the use of the shampoos.

Examples 13 to 24 and Comparative Examples 5 to 8

Body wash compositions for enhancing elasticity through skin strengthening according to Examples 13 to 24 and Comparative Examples 5 to 8 were prepared with compositions and contents shown in Tables 5 and 6. The initial elasticity of artificial skin was measured, the elasticity of artificial skin after 30 times of use was assessed using each composition prepared previously, and the skin elasticity enhancement effect of the compositions were compared.

TABLE 5

| (Parts by weight) | Example 1 | Example 2 | Example 3 | Example 4 | Example 5 | Example 6 |
|---|---|---|---|---|---|---|
| Water | To 100 | To 100 | To 100 | To 100 | To 100 | To 100 |
| Polyquaternium-7 | 0.5 | 0.5 | 0.5 | 0.5 | 0.5 | 0.5 |
| EDTA 4Na | 0.05 | 0.05 | 0.05 | 0.05 | 0.05 | 0.05 |
| Lauric Acid | 3 | 3 | 3 | 3 | 3 | 3 |
| Myristic acid | 4 | 4 | 4 | 4 | 4 | 4 |
| Sodium Lauryl Ether (2 mole) Sulfate (30%) | 20 | 20 | 20 | 20 | 20 | 20 |
| Cocamidopropyl Betaine (30%) | 15 | 15 | 15 | 15 | 15 | 15 |
| Fragrance | 0.9 | 0.9 | 0.9 | 0.9 | 0.9 | 0.9 |
| 3-aminopropyltriethoxysilane | 0.5 | — | — | — | 0.5 | — |
| 3-aminopropylmethyldiethoxysilane | — | 0.5 | — | — | — | 0.5 |
| 3-aminopropyldimethylethoxysilane | — | — | 0.5 | — | — | — |
| p-aminophenyltriethoxysilane | — | — | — | 0.5 | — | — |
| Benzene, 1,3-bis(1-isocyanato-1-methylethyl)-, homopolymer, polyethylene glycol mono-Me-ether-blocked | 1 | 1 | 1 | 1 | — | — |
| 1,1'-methylene-bis-(4-isocyanatocyclohexane)-, homopolymer, polyethylene glycol mono-Me-ether-blocked | — | — | — | — | 1 | 1 |
| N-[(1H-benzotriazole-1-yl)(dimethylamino)methylene]-N-methylmethaneaminium hexafluorophosphate N-oxide | — | — | — | — | — | — |

TABLE 5-continued

| (Parts by weight) | | | | | | |
|---|---|---|---|---|---|---|
| Benzotriazole-1-yloxytris(dimethylamino)phosphonium hexafluorophosphate | — | — | — | — | — | — |
| pH adjustor | q.s. | q.s. | q.s. | q.s. | q.s. | q.s. |
| Total | 100 | 100 | 100 | 100 | 100 | 100 |

| (Parts by weight) | Example 7 | Example 8 | Example 9 | Example 10 | Example 11 | Example 12 |
|---|---|---|---|---|---|---|
| Water | To 100 | To 100 | To 100 | To 100 | To 100 | To 100 |
| Polyquaternium-7 | 0.5 | 0.5 | 0.5 | 0.5 | 0.5 | 0.5 |
| EDTA 4Na | 0.05 | 0.05 | 0.05 | 0.05 | 0.05 | 0.05 |
| Lauric Acid | 3 | 3 | 3 | 3 | 3 | 3 |
| Myristic acid | 4 | 4 | 4 | 4 | 4 | 4 |
| Sodium Lauryl Ether (2 mole) Sulfate (30%) | 20 | 20 | 20 | 20 | 20 | 20 |
| Cocamidopropyl Betaine (30%) | 15 | 15 | 15 | 15 | 15 | 15 |
| Fragrance | 0.9 | 0.9 | 0.9 | 0.9 | 0.9 | 0.9 |
| 3-aminopropyltriethoxysilane | — | — | 0.2 | 0.2 | 0.5 | 0.5 |
| 3-aminopropylmethyldiethoxysilane | — | — | 0.2 | 0.2 | — | — |
| 3-aminopropyldimethylethoxysilane | 0.5 | — | 0.2 | 0.2 | — | — |
| p-aminophenyltriethoxysilane | — | 0.5 | 0.2 | 0.2 | — | — |
| Benzene,1,3-bis(1-isocyanato-1-methylethyl)-, homopolymer, polyethylene glycol mono-Me-ether-blocked | — | — | — | 0.5 | — | — |
| 1,1'-methylene-bis-(4-isocyanatocyclohexane)-, homopolymer, polyethylene glycol mono-Me-ether-blocked | 1 | 1 | 1 | 0.5 | — | — |
| N-[(1H-benzotriazole-1-yl)(dimethylamino)methylene]-N-methylmethaneaminium hexafluorophosphate N-oxide | — | — | — | — | 1 | — |
| Benzotriazole-1-yloxytris(dimethylamino)phosphonium hexafluorophosphate | — | — | — | — | — | 1 |
| pH adjustor | q.s. | q.s. | q.s. | q.s. | q.s. | q.s. |
| Total | 100 | 100 | 100 | 100 | 100 | 100 |

TABLE 6

| (Parts by weight) | Comparative Example 5 | Comparative Example 6 | Comparative Example 7 | Comparative Example 8 |
|---|---|---|---|---|
| Water | To 100 | To 100 | To 100 | To 100 |
| Polyquaternium-7 | 0.5 | 0.5 | 0.5 | 0.5 |
| EDTA 4Na | 0.05 | 0.05 | 0.05 | 0.05 |
| Lauric Acid | 3 | 3 | 3 | 3 |
| Myristic acid | 4 | 4 | 4 | 4 |
| Sodium Lauryl Ether (2 mole) Sulfate (30%) | 20 | 20 | 20 | 20 |
| Cocamidopropyl Betaine (30%) | 15 | 15 | 15 | 15 |
| Fragrance | 0.9 | 0.9 | 0.9 | 0.9 |
| 3-aminopropyltriethoxysilane | 0.5 | — | — | — |
| 3-aminopropylmethyldiethoxysilane | — | 0.5 | — | — |
| 3-aminopropyldimethylethoxysilane | — | — | 0.5 | — |
| p-aminophenyltriethoxysilane | — | — | — | 0.5 |

TABLE 6-continued

| (Parts by weight) | Comparative Example 5 | Comparative Example 6 | Comparative Example 7 | Comparative Example 8 |
|---|---|---|---|---|
| Benzene, 1,3-bis(1-isocyanato-1-methylethyl)-, homopolymer, polyethylene glycol mono-Me-ether-blocked | — | — | — | — |
| 1,1'-methylene-bis-(4-isocyanatocyclohexane)-, homopolymer, polyethylene glycol mono-Me-ether-blocked | — | — | — | — |
| N-[(1H-benzotriazole-1-yl)(dimethylamino)methylene]-N-methylmethaneaminium hexafluorophosphate N-oxide | — | — | — | — |
| Benzotriazole-1-yloxytris(dimethylamino) phosphonium hexafluorophosphate | — | — | — | — |
| pH adjustor | q.s. | q.s. | q.s. | q.s. |
| Total | 100 | 100 | 100 | 100 |

TABLE 7

| | Example 13 | Example 14 | Example 15 | Example 16 | Example 17 | Example 18 |
|---|---|---|---|---|---|---|
| Skin elasticity increase rate (%) | 23.2 | 22.1 | 22 | 20.9 | 23.1 | 22.3 |

| | Example 19 | Example 20 | Example 21 | Example 22 | Example 23 | Example 24 |
|---|---|---|---|---|---|---|
| Skin elasticity increase rate (%) | 22.1 | 20 | 33.4 | 34.7 | 21.7 | 22.2 |

TABLE 8

| | Comparative Example 5 | Comparative Example 6 | Comparative Example 7 | Comparative Example 8 |
|---|---|---|---|---|
| Skin elasticity increase rate (%) | 10.2 | 9.8 | 9.7 | 8.5 |

As shown in Tables 7 and 8, the experiments for the compositions according to Examples 13 to 24 and Comparative Examples 5 to 8 showed that, compared to the compositions of Comparative Examples 5 to 8 including only an amino acid component without a reaction mediator, the compositions including, as a reaction mediator, benzene, 1,3-bis(1-isocyanato-1-methylethyl)-, homopolymer, polyethylene glycol mono-Me-ether-blocked (Examples 13 to 16 and 22) or 1,1'-methylene-bis-(4-isocyanatocyclohexane)-, homopolymer, polyethylene glycol mono-Me-ether-blocked (Examples 17 to 22), N-[(1H-benzotriazole-1-yl)(dimethylamino)methylene]-N-methylmethaneaminium hexafluorophosphate N-oxide (Example 23) and benzotriazole-1-yloxytris(dimethylamino)phosphonium hexafluorophosphate (Example 24) exhibit a very excellent skin elasticity improvement effect after the use of the body washes.

Examples 25 to 36 and Comparative Examples 9 to 12

Compositions for strengthening nails according to Examples 25 to 36 and Comparative Examples 9 to 12 were prepared with compositions and contents shown in Tables 9 and 10 below. Each composition was used on 10 consumers for 20 days, and then conditions of nails such as splitting or cracking were compared to those of the initial conditions of the nails, and sensory evaluated on a 5-point scale (5: very good, 4: good, 3: no difference, 2: almost no effect, 1: no effect at all) for comparison.

TABLE 9

| (Parts by weight) | Example 25 | Example 26 | Example 27 | Example 28 | Example 29 | Example 30 |
|---|---|---|---|---|---|---|
| Water | To 100 | To 100 | To 100 | To 100 | To 100 | To 100 |
| Amodimethicone | 0.5 | 0.5 | 0.5 | 0.5 | 0.5 | 0.5 |
| 18-Methyl Eicosanoic Acid | 1 | 1 | 1 | 1 | 1 | 1 |
| Isostearylamine | 1 | 1 | 1 | 1 | 1 | 1 |
| Glycerin | 2 | 2 | 2 | 2 | 2 | 2 |
| Butylene glycol | 2 | 2 | 2 | 2 | 2 | 2 |
| Propylene glycol | 2 | 2 | 2 | 2 | 2 | 2 |
| Fragrance | 0.9 | 0.9 | 0.9 | 0.9 | 0.9 | 0.9 |
| Carboxyvinyl polymer | 0.1 | 0.1 | 0.1 | 0.1 | 0.1 | 0.1 |
| Polysolvate 60 | 1.5 | 1.5 | 1.5 | 1.5 | 1.5 | 1.5 |
| Liquid paraffin | 5 | 5 | 5 | 5 | 5 | 5 |
| Caprylic/capric triglyceride | 2.5 | 2.5 | 2.5 | 2.5 | 2.5 | 2.5 |
| Squalane | 2.5 | 2.5 | 2.5 | 2.5 | 2.5 | 2.5 |

TABLE 9-continued

| (Parts by weight) | | | | | | |
|---|---|---|---|---|---|---|
| Cetearyl glucoside | 2 | 2 | 2 | 2 | 2 | 2 |
| Triethanolamine | 0.1 | 0.1 | 0.1 | 0.1 | 0.1 | 0.1 |
| 3-aminopropyltriethoxysilane | 0.5 | — | — | — | 0.5 | — |
| 3-aminopropylmethyldiethoxysilane | — | 0.5 | — | — | — | 0.5 |
| 3-aminopropyldimethylethoxysilane | — | — | 0.5 | — | — | — |
| p-aminophenyltriethoxysilane | — | — | — | 0.5 | — | — |
| Benzene, 1,3-bis(1-isocyanato-1-methylethyl)-, homopolymer, polyethylene glycol mono-Me-ether-blocked | 1 | 1 | 1 | 1 | — | — |
| 1,1'-methylene-bis-(4 isocyanatocyclohexane)-, homopolymer, polyethylene glycol mono-Me-ether-blocked | — | — | — | — | 1 | 1 |
| N-[(1H-benzotriazole-1-yl)(dimethylamino)methylene]-N-methylmethaneaminium hexafluorophosphate N-oxide | — | — | — | — | — | — |
| Benzotriazole-1-yloxytris(dimethylamino)phosphonium hexafluorophosphate | — | — | — | — | — | — |
| pH adjustor | q.s. | q.s. | q.s. | q.s. | q.s. | q.s. |
| Total | 100 | 100 | 100 | 100 | 100 | 100 |

| (Parts by weight) | Example 31 | Example 32 | Example 33 | Example 34 | Example 35 | Example 36 |
|---|---|---|---|---|---|---|
| Water | To 100 | To 100 | To 100 | To 100 | To 100 | To 100 |
| Amodimethicone | 0.5 | 0.5 | 0.5 | 0.5 | 0.5 | 0.5 |
| 18-Methyl Eicosanoic Acid | 1 | 1 | 1 | 1 | 1 | 1 |
| Isostearylamine | 1 | 1 | 1 | 1 | 1 | 1 |
| Glycerin | 2 | 2 | 2 | 2 | 2 | 2 |
| Butylene glycol | 2 | 2 | 2 | 2 | 2 | 2 |
| Propylene glycol | 2 | 2 | 2 | 2 | 2 | 2 |
| Fragrance | 0.9 | 0.9 | 0.9 | 0.9 | 0.9 | 0.9 |
| Carboxyvinyl polymer | 0.1 | 0.1 | 0.1 | 0.1 | 0.1 | 0.1 |
| Polysolvate 60 | 1.5 | 1.5 | 1.5 | 1.5 | 1.5 | 1.5 |
| Liquid paraffin | 5 | 5 | 5 | 5 | 5 | 5 |
| Caprylic/capric triglyceride | 2.5 | 2.5 | 2.5 | 2.5 | 2.5 | 2.5 |
| Squalane | 2.5 | 2.5 | 2.5 | 2.5 | 2.5 | 2.5 |
| Cetearyl glucoside | 2 | 2 | 2 | 2 | 2 | 2 |
| Triethanolamine | 0.1 | 0.1 | 0.1 | 0.1 | 0.1 | 0.1 |
| 3-aminopropyltriethoxysilane | — | — | 0.2 | 0.2 | 0.5 | 0.5 |
| 3-aminopropylmethyldiethoxysilane | — | — | 0.2 | 0.2 | — | — |
| 3-aminopropyldimethylethoxysilane | 0.5 | — | 0.2 | 0.2 | — | — |
| p-aminophenyltriethoxysilane | — | 0.5 | 0.2 | 0.2 | — | — |
| Benzene, 1,3-bis(1-isocyanato-1-methylethyl)-, homopolymer, polyethylene glycol mono-Me-ether-blocked | — | — | — | 0.5 | — | — |
| 1,1'-methylene-bis-(4 isocyanatocyclohexane)-, homopolymer, polyethylene glycol mono-Me-ether-blocked | 1 | 1 | 1 | 0.5 | — | — |

TABLE 9-continued

| | | | | | | |
|---|---|---|---|---|---|---|
| N-[(1H-benzotriazole-1-yl)(dimethylamino)methylene]-N-methylmethaneaminium hexafluorophosphate N-oxide | — | — | — | — | 1 | — |
| Benzotriazole-1-yloxytris(dimethylamino)phosphonium hexafluorophosphate | — | — | — | — | — | 1 |
| pH adjustor | q.s. | q.s. | q.s. | q.s. | q.s. | q.s. |
| Total | 100 | 100 | 100 | 100 | 100 | 100 |

TABLE 10

| (Parts by weight) | Comparative Example 9 | Comparative Example 10 | Comparative Example 11 | Comparative Example 12 |
|---|---|---|---|---|
| Water | To 100 | To 100 | To 100 | To 100 |
| Amodimethicone | 0.5 | 0.5 | 0.5 | 0.5 |
| 18-Methyl Eicosanoic Acid | 1 | 1 | 1 | 1 |
| Isostearylamine | 1 | 1 | 1 | 1 |
| Glycerin | 2 | 2 | 2 | 2 |
| Butylene glycol | 2 | 2 | 2 | 2 |
| Propylene glycol | 2 | 2 | 2 | 2 |
| Fragrance | 0.9 | 0.9 | 0.9 | 0.9 |
| Carboxyvinyl polymer | 0.1 | 0.1 | 0.1 | 0.1 |
| Polysolvate 60 | 1.5 | 1.5 | 1.5 | 1.5 |
| Liquid paraffin | 5 | 5 | 5 | 5 |
| Caprylic/caprictriglyceride | 2.5 | 2.5 | 2.5 | 2.5 |
| Squalane | 2.5 | 2.5 | 2.5 | 2.5 |
| Cetearyl glucoside | 2 | 2 | 2 | 2 |
| triethanolamine | 0.1 | 0.1 | 0.1 | 0.1 |
| 3-aminopropyltriethoxysilane | 0.5 | — | — | — |
| 3-aminopropylmethyldiethoxysilane | — | 0.5 | — | — |
| 3-aminopropyldimethylethoxysilane | — | — | 0.5 | — |
| p-aminophenyltriethoxysilane | — | — | — | 0.5 |
| Benzene, 1,3-bis(1-isocyanato-1-methylethyl)-, homopolymer, polyethylene glycol mono-Me-ether-blocked | — | — | — | — |
| 1,1'-methylene-bis-(4-isocyanatocyclohexane)-, homopolymer, polyethylene glycol mono-Me-ether-blocked | — | — | — | — |
| N-[(1H-benzotriazole-1-yl)(dimethylamino)methylene]-N-methylmethaneaminium hexafluorophosphate N-oxide | — | — | — | — |
| Benzotriazole-1-yloxytris(dimethylamino)phosphonium hexafluorophosphate | — | — | — | — |
| pH adjustor | q.s. | q.s. | q.s. | q.s. |
| Total | 100 | 100 | 100 | 100 |

TABLE 11

| | Example 25 | Example 26 | Example 27 | Example 28 | Example 29 | Example 30 |
|---|---|---|---|---|---|---|
| Satisfaction of nail strength improvement effect (5-point scale) | 3.7 | 3.7 | 3.6 | 3.8 | 4.1 | 4 |

| | Example 31 | Example 32 | Example 33 | Example 34 | Example 35 | Example 36 |
|---|---|---|---|---|---|---|
| Satisfaction of nail strength improvement effect (5-point scale) | 4 | 3.9 | 4.2 | 4.4 | 3.6 | 3.6 |

TABLE 12

| | Comparative Example 9 | Comparative Example 10 | Comparative Example 11 | Comparative Example 12 |
|---|---|---|---|---|
| Satisfaction of nail strength improvement effect (5-point scale) | 2.2 | 2.4 | 2.2 | 2.1 |

As shown in Tables 11 and 12, experiments for the compositions according to Examples 25 to 36 and Comparative Examples 9 to 12 showed that, compared to the compositions of Comparative Examples 9 to 12 including only an amino acid component without a reaction mediator, the compositions including, as a reaction mediator, benzene, 1,3-bis(1-isocyanato-1-methylethyl)-, homopolymer, polyethylene glycol mono-Me-ether-blocked (Examples 25 to 28 and 34) or 1,1'-methylene-bis-(4-isocyanatocyclohexane)-, homopolymer, polyethylene glycol mono-Me-ether-blocked (Examples 29 to 34), N-[(1H-benzotriazole-1-yl)(dimethylamino)methylene]-N-methylmethaneaminium hexafluorophosphate N-oxide (Example 35), and benzotriazole-1-yloxytris(dimethylamino)phosphonium hexafluorophosphate (Example 36) exhibit a very excellent nail strength enhancement effect.

The invention claimed is:

1. A method for enhancing protein strength, comprising:
treating a protein with a composition comprising an aminosilane compound, and a carbodiimide-based compound, and solvent consisting of water,
wherein the protein is selected from the group consisting of hair, skin, finger nails, and toe nails,
the aminosilane compound is selected from the group consisting of the compounds represented by Formulas 1 to 3:

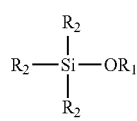

[Formula 1]

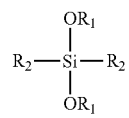

[Formula 2]

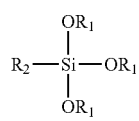

[Formula 3]

wherein in Formulas 1 to 3,
$R_1$ is each independently hydrogen; or a linear, branched or cyclic hydrocarbon having 1 to 500 carbon atoms or a benzene ring hydrocarbon, which includes one or more double bonds, or is optionally substituted with one or more atoms selected from the group consisting of O, N, S, P and Si, or substituted in an anionic, cationic or amphoteric form, or includes a structure to which a metal ion is bonded in a salt form; and $R_2$ is each independently a linear, branched or cyclic hydrocarbon having 1 to 500 carbon atoms or a benzene ring hydrocarbon, which includes one or more double bonds, or is optionally substituted with one or more atoms selected from the group consisting of O, N, S, P and Si, or substituted in an anionic, cationic or amphoteric form, or includes a structure to which a metal ion is bonded in a salt form, and in which at least one primary or secondary amine is included at an end of the molecular structure, and the carbodiimide-based compound is represented by Formula 4 below, or a salt form thereof formed by bonding with a metal ion:

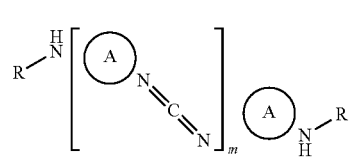

[Formula 4]

wherein in Formula 4,
A each independently represents a monomer selected from structures listed below,

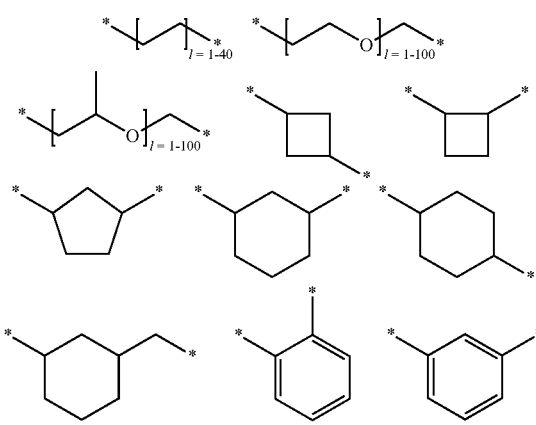

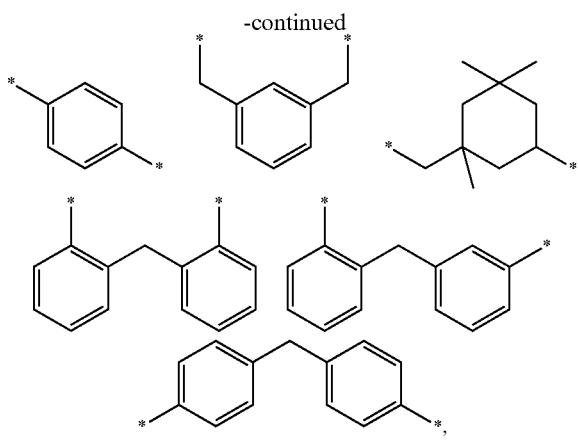

wherein * denotes a connecting position,

R each independently represents hydrogen; or C1 to C500 linear, branched or cyclic hydrocarbon; or an aromatic hydrocarbon, which includes one or more double bonds, or is optionally substituted with one or more atoms selected from the group consisting of O, N, S, P and Si, and m is an integer of 1 to 100, and when m is 2 or greater, each of

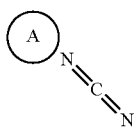

is the same or different from each other.

2. The method according to claim 1, wherein the aminosilane compound is one or more selected from the group consisting of 3-aminopropyltriethoxysilane, bis[(3-triethoxysilyl)propyl] amine, 3-aminopropyltrimethoxysilane, 4-aminobutyltriethoxysilane, bis[(3-trimethoxysilyl)propyl] amine, 3-aminopropylmethyldiethoxysilane, 3-aminopropyldimethylethoxysilane, 3-aminopropylmethyldimethoxysilane, aminoethylaminopropyltrimethoxysilane, aminoethylaminopropyltriethoxysilane, aminoethylaminopropylmethyldimethoxysilane, diethylenetriaminopropylmethyldimethoxysilane, piperazinylpropylmethyldimethoxysilane, (n-phenylamino)methyltrimethoxysilane, (n-phenylamino)methyltriethoxysilane, 3-(n-phenylamino)propyltrimethoxysilane, n-(n-butyl)-3-aminopropyltrimethoxysilane, 4-aminobutyltriethoxysilane, m-aminophenyltrimethoxysilane, p-aminophenyltrimethoxysilane, aminophenyltrimethoxysilane, m-aminophenyltriethoxysilane, p-aminophenyltriethoxysilane, aminophenyltriethoxysilane, 3-aminopropyltris (methoxyethoxy-ethoxy)silane, 11-aminoundecyltriethoxysilane, 3-(m-aminophenoxy(propyltrimethoxy-silane), aminopropylsilanetriol, 3-aminopropylmethyldiethoxysilane, 3-aminopropyldiisopropylethoxysilane, 3-aminopropyldimethylethoxysilane, n-(2-aminoethyl)-3-aminopropyltri-methoxysilane, n-(2-aminoethyl)-3-aminopropyltri-ethoxysilane, n-(6-aminohexyl)aminomethyl-triethoxysilane, n-(6-aminohexyl)aminopropyl-trimethoxysilane, n-(2-aminoethyl)-11-aminoundecyl-trimethoxysilane, (amino ethylaminomethyl)phenethyl-trimethoxysilane, n-3-amino (polypropylenoxy)]amino-propyltrimethoxy silane, n-(2-aminoethyl)-3-aminopropyl-silanetrio 1, n-(2-aminoethyl)-3-aminopropylmethyl-dimethoxysilane, n-(2-aminoethyl)-3-aminoisobutyl-methyldimethoxysilane, (amino ethylamino)-3-isobutyldi-methylmethoxysilane, (3-trimethoxysilylpropyl)diethylene-triamine, n-butylaminopropyltrimethoxy-silane, n-ethylaminoisobutylt-rimethoxy-silane, n-methyl aminopropyltrimethoxy-silane, n-phenylaminopropyltrimethoxy-silane, 3-(n-allylamino) propyltrimethoxy-silane, (cyclohexylaminomethyl)triethoxysilane, n-cyclohexylaminopropyltrimeth-oxysilane, n-ethylaminoisobutylmethyl-diethoxysilane, (phenylaminomethyl)methyl-dimethoxysilane, n-phenylaminomethyl-triethoxysilane, n-methylaminopropylmethyl-dimethoxy silane, 3-(n-styrylmethyl-2-aminoethylamino)-propyltrimethoxysilane hydrochloride, n-(trimethoxysilylpropyl) isothio-uronium chloride, bis[(3-trimethoxysilyl)propyl]-ethylenediamine, bis[(3-trimethoxysilyl)propyl]-ethylenediamine, bis[3-(triethoxysilyl)propyl]urea, bis (trimethoxysilylpropyl)urea, bis(methyldiethoxysilylpropyl) amine, ureidopropyltriethoxysilane, acetamidopropyltrimethoxysilane, n-[5-(trimethoxysilyl)-2-aza-1-oxo-pentyl]caprolactam and ureidopropyltrimethoxysilane.

3. The method according to claim 1, wherein the aminosilane compound is contained at 0.000001 to 30 parts by weight with respect to 100 parts by weight of the total composition.

4. The method according to claim 1, wherein the carbodiimide-based compound is contained at 0.001 to 20 parts by weight with respect to 100 parts by weight of the total composition.

* * * * *